(12) United States Patent
Rassman

(10) Patent No.: US 6,572,625 B1
(45) Date of Patent: Jun. 3, 2003

(54) HAIR TRANSPLANT HARVESTING DEVICE AND METHOD FOR ITS USE

(76) Inventor: William R. Rassman, 9911 W. Pico, suite 301, Los Angeles, CA (US) 90035

( * ) Notice: Subject to any disclaimer, the term of this patent is extended or adjusted under 35 U.S.C. 154(b) by 0 days.

(21) Appl. No.: 09/567,914

(22) Filed: May 10, 2000

Related U.S. Application Data

(63) Continuation of application No. 09/146,739, filed on Sep. 13, 1998.

(51) Int. Cl.⁷ .................................................. A61B 17/32
(52) U.S. Cl. .................................... 606/133; 606/184
(58) Field of Search ......................... 606/133, 184, 606/187; 600/566, 567

(56) References Cited

U.S. PATENT DOCUMENTS

| | | | | |
|---|---|---|---|---|
| 4,476,864 A | * | 10/1984 | Tezel | 606/184 |
| 5,693,064 A | * | 12/1997 | Arnold | 606/184 |
| 5,792,163 A | * | 8/1998 | Hitzig | 606/184 |
| 5,827,199 A | * | 10/1998 | Alexander | 606/184 |

\* cited by examiner

*Primary Examiner*—Michael H. Thaler
(74) *Attorney, Agent, or Firm*—Herbert M. Shapiro

(57) ABSTRACT

The harvesting of hair for a hair transplant procedure employs a hollow drill with an imaging system which permits alignment of center of the cutting edge of the needle with the axis of the follicular unit to be removed. The diameter of the needle is chosen such that when properly aligned, a follicular unit is removed without damaging critical anatomical portions of the follicles. In one embodiment, fluid is introduced to separate adjacent follicles. In another embodiment, suction is applied to aid in the removal of the excised follicular unit. In still another embodiment, an x/y/z stabilizing gantry is employed to position the hollow needle in each instance.

17 Claims, 6 Drawing Sheets

HAIR TRANSPLANT HARVESTING DEVICE AND METHOD FOR ITS USE

REFERENCE TO RELATED APPLICATIONS

The present application is a Continuation of application Ser. No. 09/146,739 filed Sep. 3, 1998 for the present applicant.

FIELD OF THE INVENTION

This invention relates to the extraction of hair grafts from a donor area and more particularly to a device for controllably positioning a hair extraction instrument for removing follicular units of hair.

BACKGROUND OF THE INVENTION

Hair transplant procedures have been carried out for decades. Initially, a punch was used to remove a circular area of hairy skin containing ten or more follicular units (of 1–3 hairs each). The area of hairy skin replaced a like area of bald skin removed from the patient. Several of such "plugs," were placed into areas in the bald part of the head.

The circular punch was later replaced by a hollow powered drill and the space left in the donor area was left to heal naturally. Both of these prior art procedures allowed wounds to stay open for weeks at a time exposing a patient to the discomfort from large wounds measuring 3–5 millimeters in diameter.

Today's standard procedure involves a linear incision which permits a strip of hairy skin down into the fatty level of one quarter inch and measuring a number of square inches. The resulting wound is sutured closed and the strip is dissected (under a microscope), cooled in an ice bath or refrigerator and then transplanted into a bald area in needle size holes. Forceps grasp each graft and places them into holes in the bald area.

In one form of automatic harvesting, the harvesting of grafts from the strip of hairy skin can result in significant damage to the hair. The damage occurs because the hair in the hairy skin is forced through a cutting grid in order to make grafts of a predetermined size. The cutting blades of the grid are positioned at the most ideal distance between follicles. Unfortunately, the distance between follicles varies randomly. The result is that a significant number of the hair follicles are damaged and die.

BRIEF DESCRIPTION OF THE INVENTION

In accordance with the principles of the present invention, a hollow instrument with a cutting edge such as a drill or punch with a diameter slightly larger than a follicular unit is used to cut the scalp. The instrument includes an imaging system such as a video system which allows the health care professional to align the instrument along the axis of the follicular unit and to produce a cutting action outside of the follicular unit's critical anatomical parts. As the wound is very small, this results in relatively fast healing, less bleeding and virtually no grossly visible scar tissue formation.

In accordance with one embodiment of this invention, a fluid injection system injects fluid under high pressure into the scalp to enlarge the distance between follicular units from an average of 1 mm to about 2 mm.

In accordance with another embodiment an x/y/z stabilization gantry is employed to fix the hollow instrument and thus the imaging system. In still another embodiment a suction device is positioned to create traction driving the cutting of a follicular unit to ensure that cutting proceeds only to a prescribed depth.

DETAILED DESCRIPTION OF ILLUSTRATIVE EMBODIMENTS OF THIS INVENTION

Figure 1:
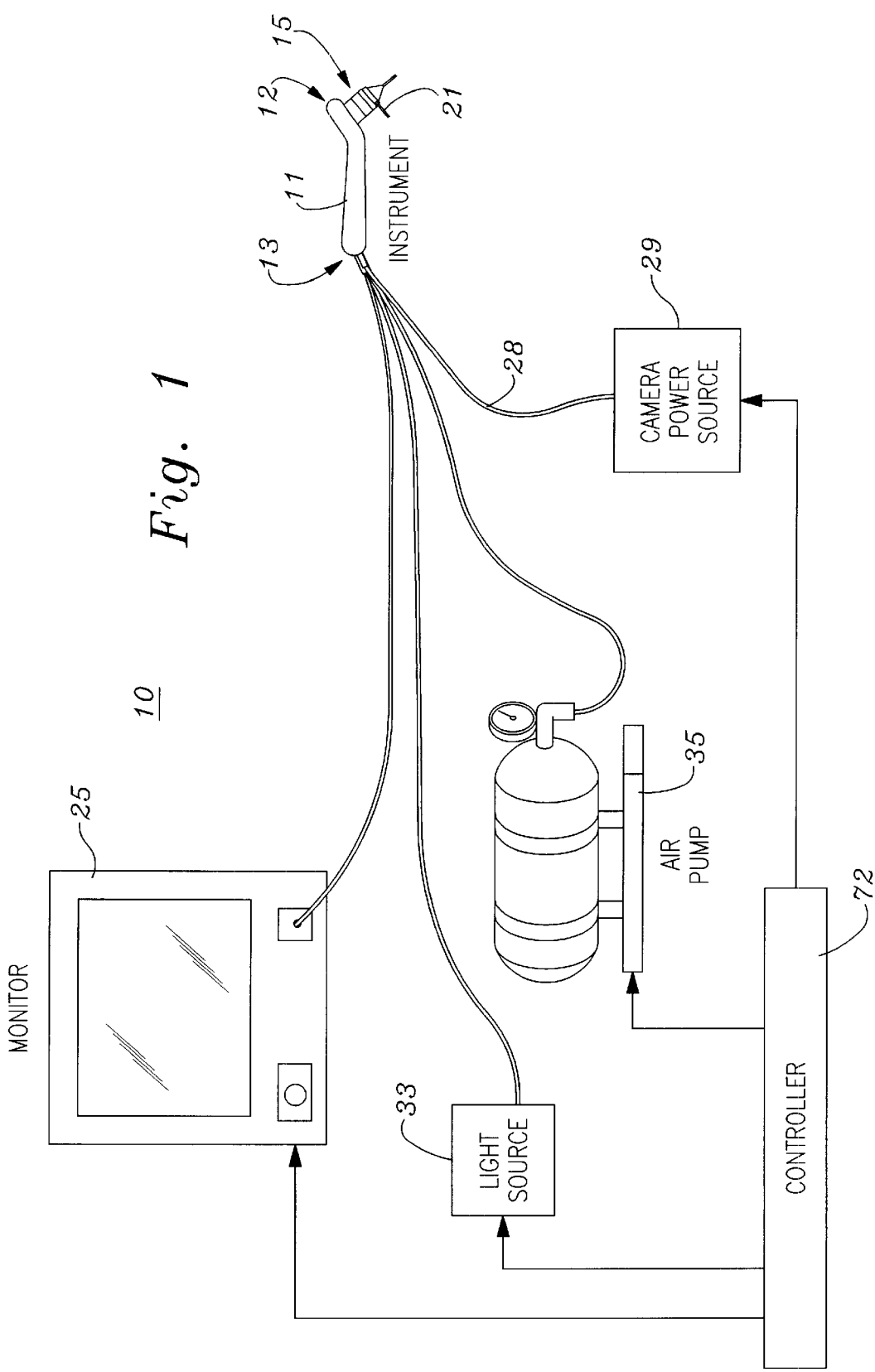
FIG. 1 is a schematic block diagram of a hair transplant harvesting device in accordance with the principles of this invention.

FIG. 1 is a block diagram of a system 10 in accordance with this invention. The system includes a hand-held instrument 11 having a proximal end and a distal end 12 and 13 respectively. A tubular shaped subassembly 15 extends from the proximal end of the instrument.

Figure 2:
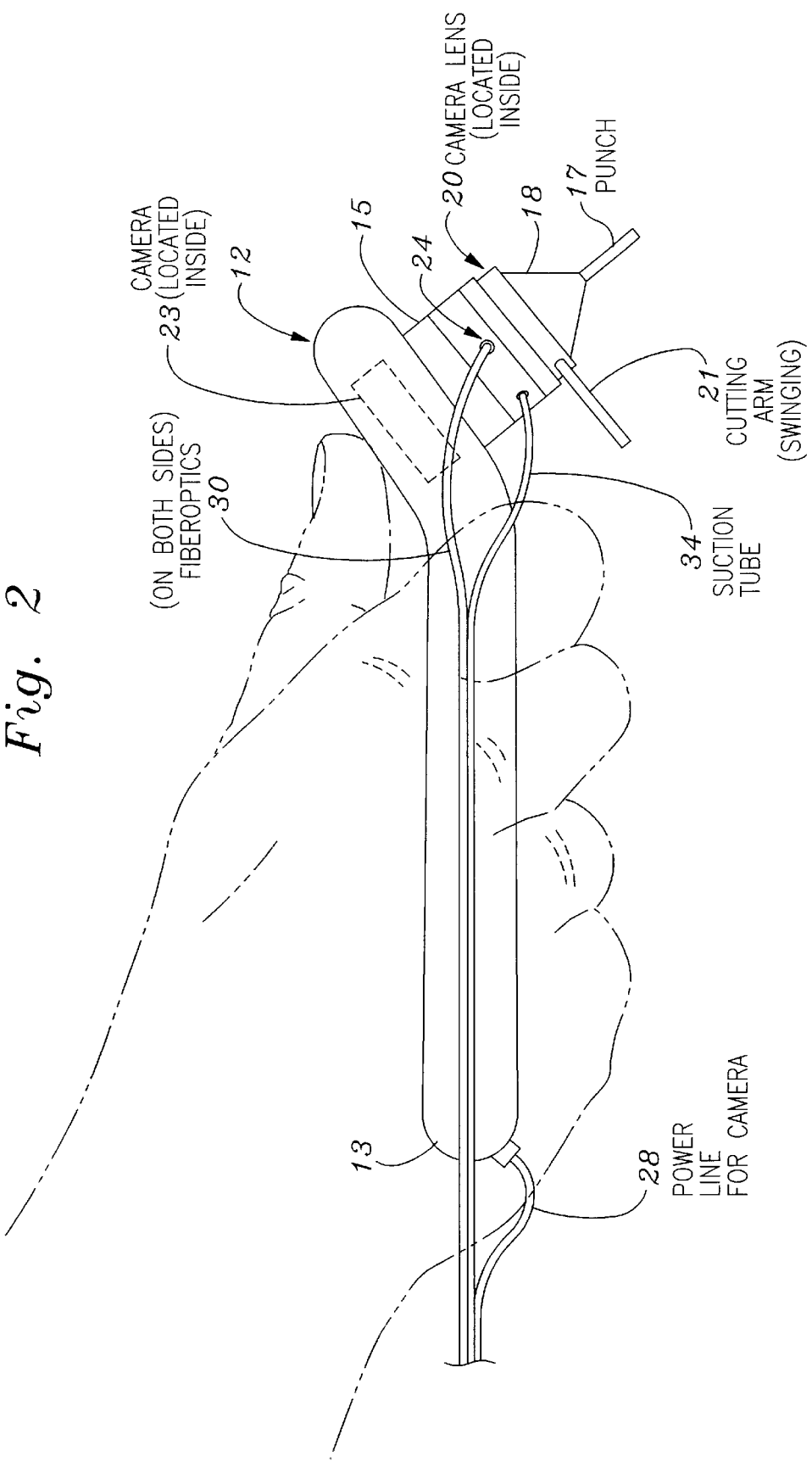
FIG. 2 is a schematic side view of a hand-held portion of the system of FIG. 1.

FIG. 2 is an enlarged schematic side view of instrument 11. Subassembly 15 can be seen to have a general shape similar to that of an instrument commonly used to examine the human ear. The subassembly includes a hollow needle or punch 17 and a conical section 18 which enlarges in diameter as it extends upwards and to the left as viewed in the figure.

The end of section 18 with the relatively large diameter is coupled to the cylindrical portion of the subassembly by a rotating member or lip 20. Rotating member 20 is operated by cutting arm 21 and serves to extend (or advance) hollow needle 17 when rotated.

Instrument 11 includes a solid state camera such as a charge-coupled device (CCD) camera represented by dashed rectangular line 23 shown in FIG. 2. Subassembly 15 also includes a lens 24. The camera and lens are components of an imaging system positioned to capture an image via the hollow needle and to display that image on monitor 25 of FIG. 1. Power for the CCD camera is provided via cable 28 of FIGS. 1 and 2 from power source 29 of FIG. 1.

Illumination of the field of view for the camera is supplied via optical fibers 30 extending from subassembly 15 to light source 33 of FIG. 1.

In one embodiment of the invention, a suction tube 34 also is provided. Tube 34 extends between subassembly 15 and an air pump 35 shown in FIG. 1. Suction may be provided to assist in extracting a follicular unit when arm 21 is rotated by a user to advance hollow needle 17 into the scalp of a patient.

Figure 3:
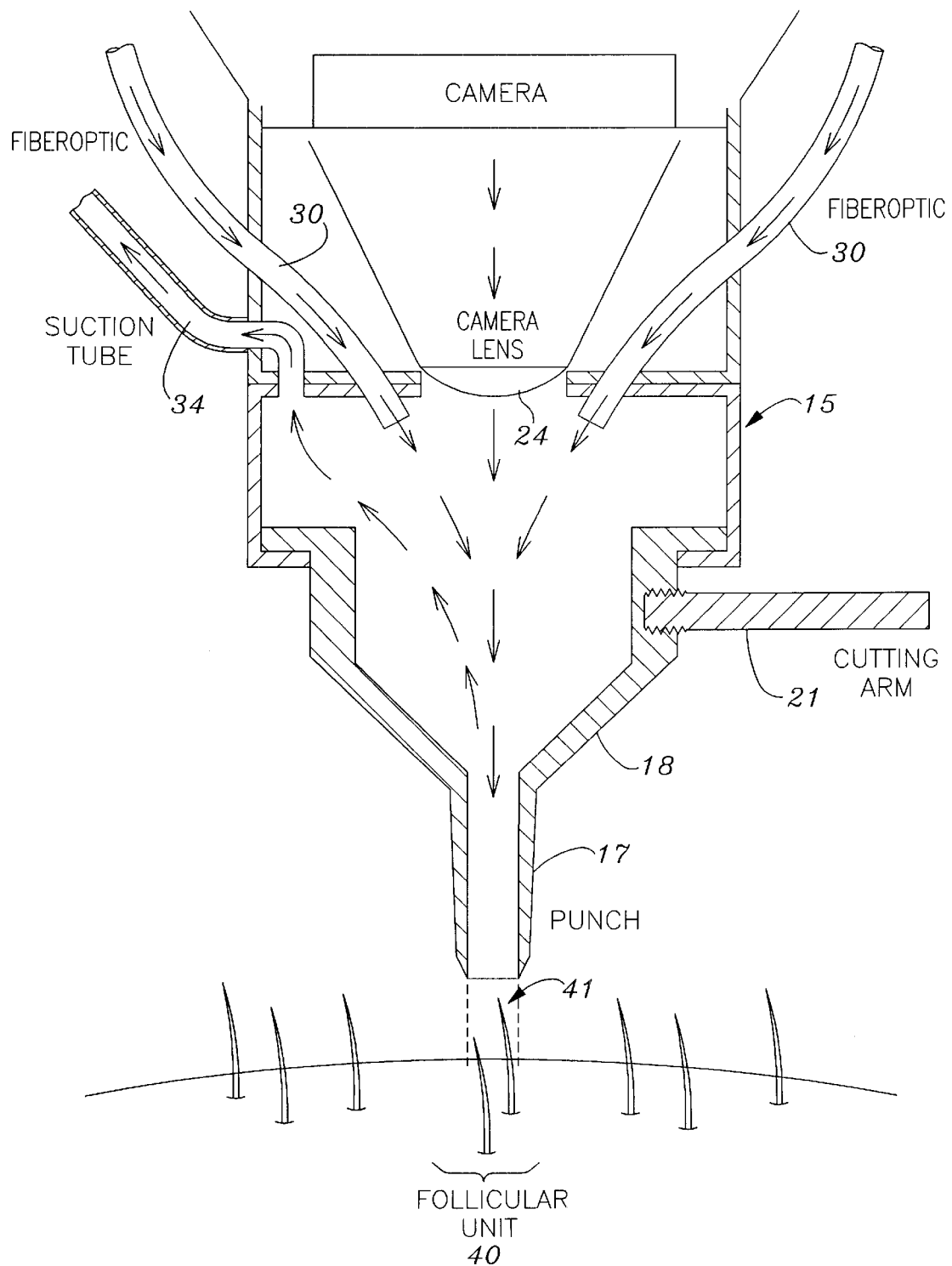
FIGS. 3 and 4 are enlarged schematic cross sectional and perspective views of a subassembly of the hand-held portion shown in FIG. 2.
Figure 4:
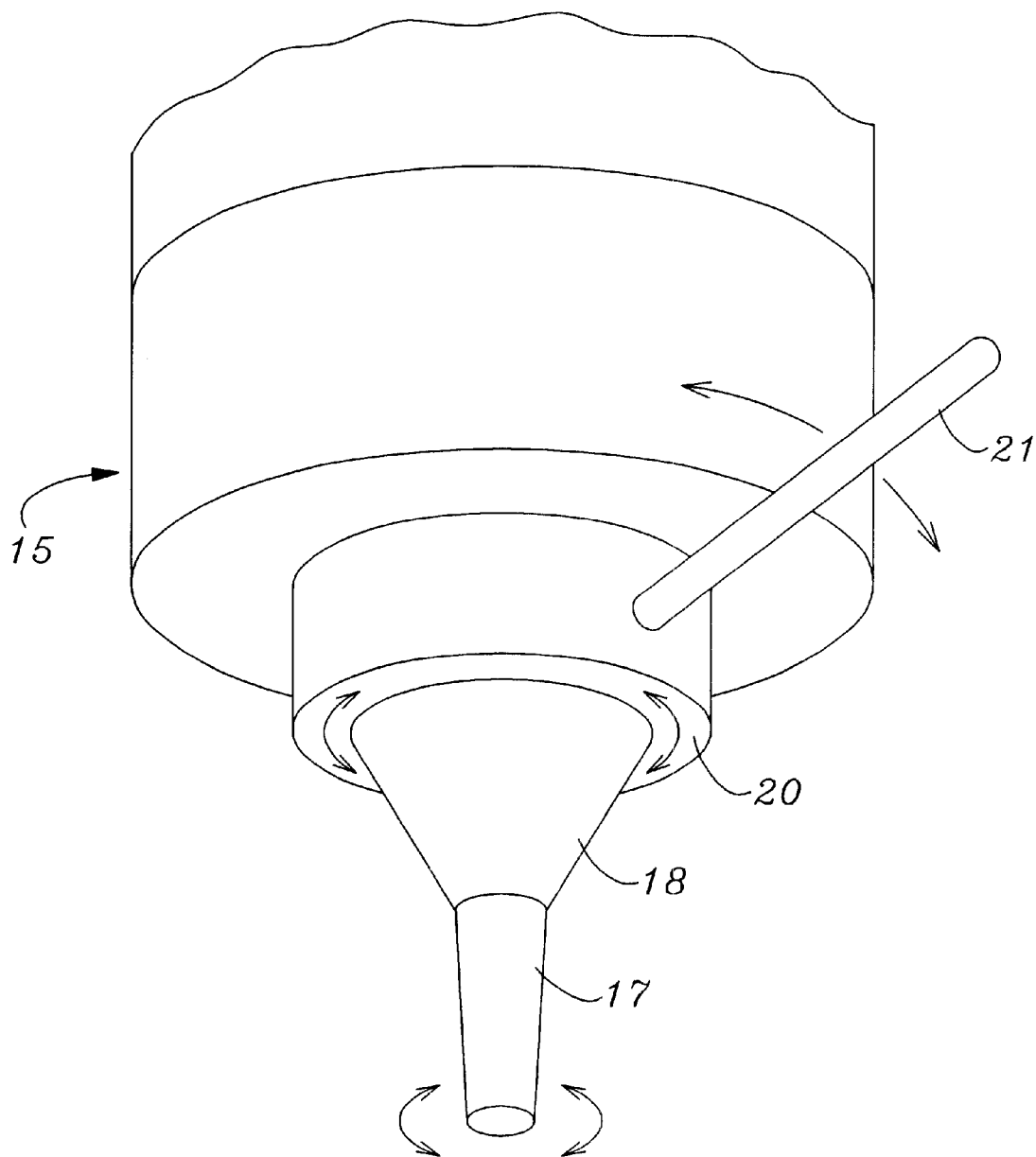

FIG. 3 shows an enlarged cross section of subassembly 15 showing the relative position of lens 24, optical fiber (30), suction tube 34, hollow needle 17, conical section 18, and rotating member 20 with cutting arm 21. FIG. 4 shows an enlarged perspective view of subassembly 15 showing hollow needle 17, conical section 18, rotating member 20 with cutting arm 21. It is clear from the views of FIGS. 3 and 4 that a user observes a follicular unit 40 as shown in FIG. 3 by moving instrument 11 (FIG. 1) until a selected follicular unit is in the center of the field of view 41. The user observes the [filed] field of view in monitor 25 of FIG. 1. The diameter of hollow needle 17 is chosen sufficiently wide to cut [past] beyond the critical anatomical structures of a follicular unit thus avoiding any damage to the unit.

Figure 5:
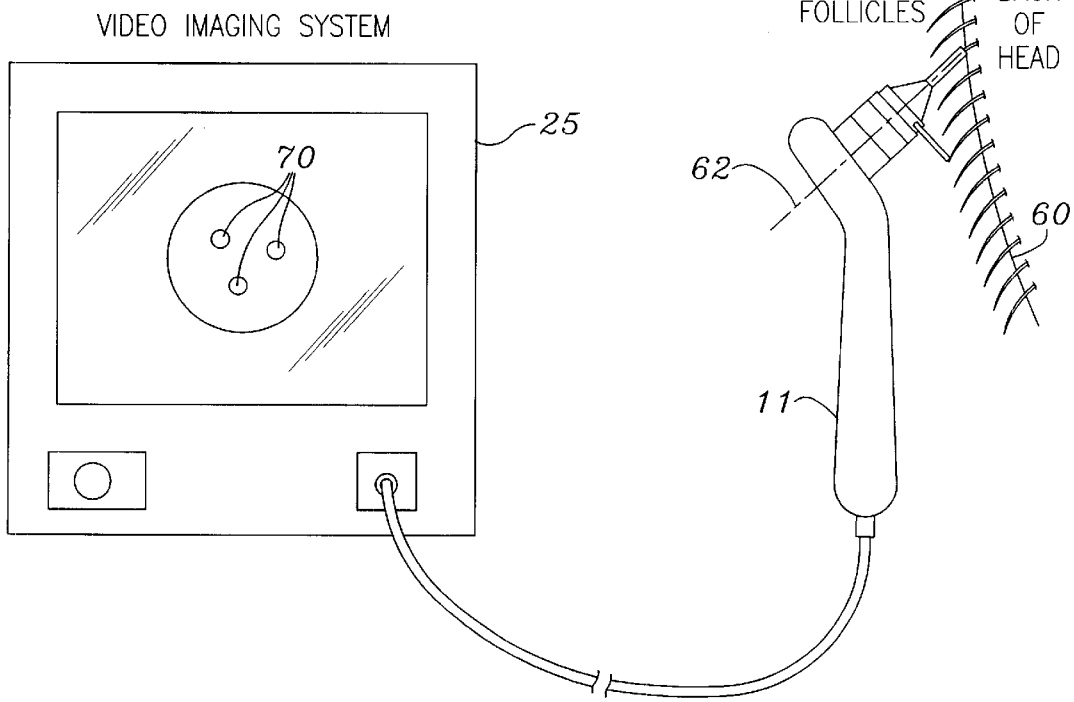
FIGS. 5 and 6 are representations of video images produced by the apparatus of FIGS. 1–4.
Figure 6:
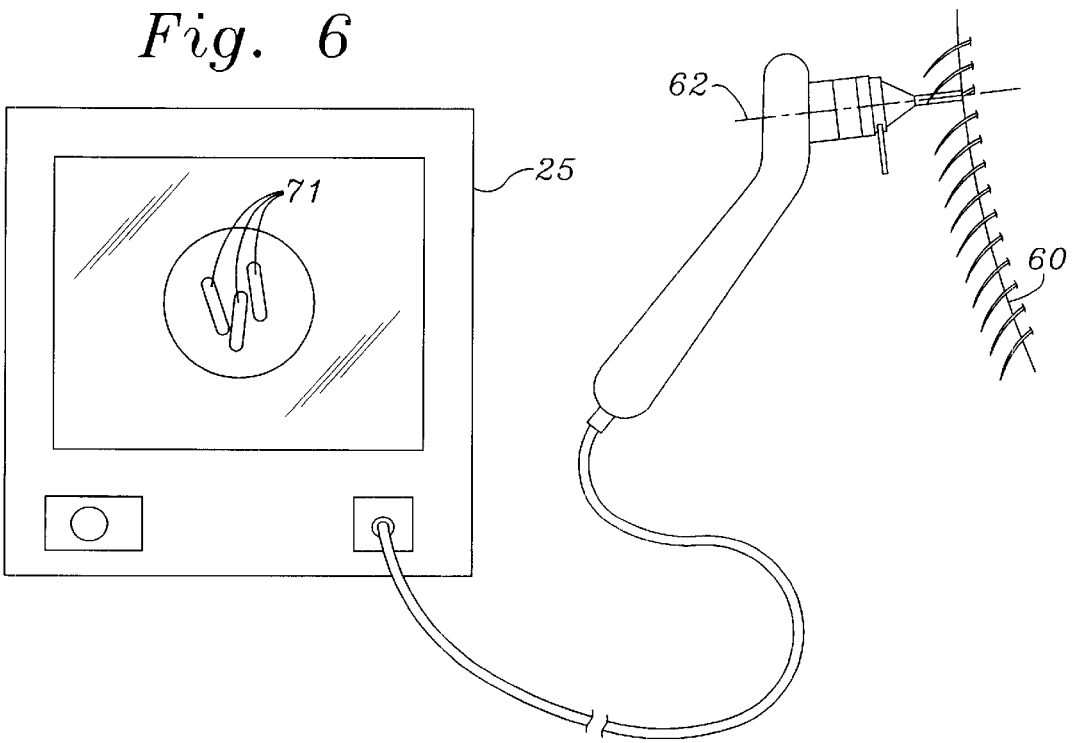

FIGS. 5 and 6 show the image of a representative follicular unit when instrument 11 is aligned with the unit and when it is not respectively. Both FIGS. 5 and 6 represent the back of a patients head 60 with hair follicules extending downwards and to the left as viewed. In FIG. 5 instrument 11 is seen to align its axis 62 with the axis of the hair follicles. In FIG. 6 the axis of instrument 11 and the hair follicles are not aligned. The resulting images in monitor 25 are dots and lines respectively.

The various components of the system of FIG. 1 may be any components capable of operating as described. The operation of the component is controlled by a controller represented by block 72 of FIG. 1.

Figure 7:
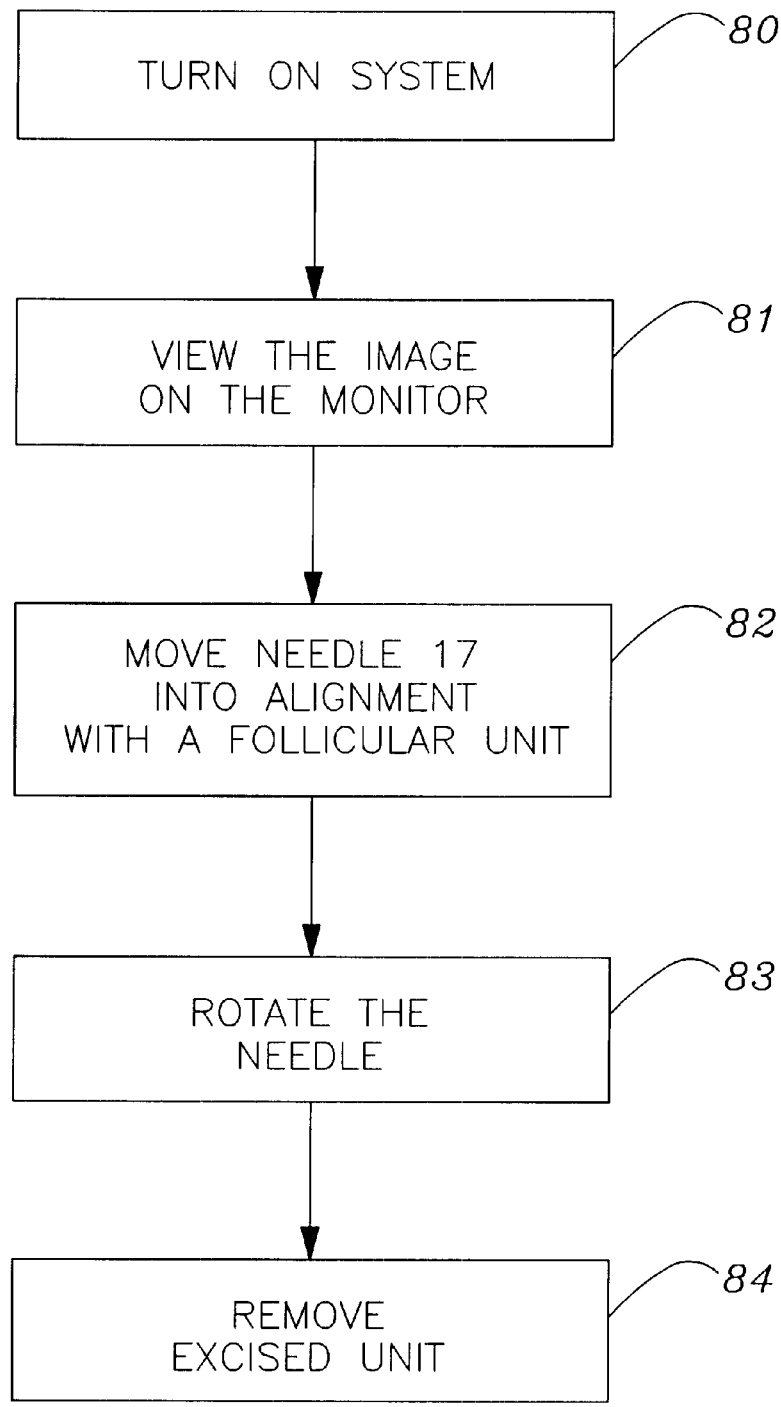
FIG. 7 is a flow diagram of the method practiced by the system of FIGS. 1–7.

FIG. 7 is a flow diagram of the method practiced by the system of FIG. 1. The system is used with a patient having a shaved head so that the donor area of the head exhibits erect hair follicles. A user positions the hollow needle over the scalp of a patient after turning on the monitor, the light source and the camera. The procedure starts by turning on the system as represented by block 80 of FIG. 7 and the image of the field of view is observed on the monitor (25) as indicated by block 81.

The user moves the instrument (11) until the field of view (illustratively through the needle) is in alignment with a follicular unit producing an image as shown in FIG. 5. This step is represented by block 82.

The instrument is now properly positioned with the top of the needle juxtaposed against the scalp of a patient with a selected follicular unit in the field of view and with the axis of the needle aligned with the axis of the follicular unit. The user now moves arm 21 to advance the needle while rotating the cutting edge of the needle to excise the unit. The rotation of the needle and the removal of the unit are represented by blocks 83 and 84.

The removal of the excised unit is expedited by the suction tube 35 and air pump assembly of FIG. 1. But any suitable method of removal is adequate. Tweezers may be used, for example.

The spacings between adjacent follicular units varies randomly but typically is greater than one millimeter. The critical anatomical structure of a unit is only a fraction of that distance thus dictating a minimum diameter of 0.50 millimeters for the hollow needle. It is thus, convenient to secure an x/y/z gantry (not shown) to the head of a patient and to secure the "hand held" instrument thus can be controlled by adjusting micromanipulators.

Further, fluid may be introduced by an injection system (not shown) to swell a target area of the scalp thus increasing the distance between follicular units in the donor area.

What is claimed is:

1. Harvesting apparatus for the removal of a single follicular unit of hair from a donor area of a patient for transplant to a bald area, said apparatus comprising a hollow instrument having a diameter with a cutting edge about equal to the diameter of critical anatomical parts of a follicular unit of hair, said apparatus including an imaging system positioned for viewing a selected follicular unit of hair, means for aligning said instrument with a selected follicular unit, and means for advancing said instrument for cutting around the selected follicular unit.

2. Apparatus as in claim 1 wherein said imaging system includes video means for viewing the image produced by said imaging system.

3. Apparatus as in claim 2 wherein said imaging system includes fiber optic means located within said instrument, said fiber optic means being energy coupled to a light source for illuminating a selected follicular unit with which said instrument is aligned.

4. Apparatus as in claim 2 wherein said imaging system includes a camera for capturing said image and means coupled to said camera for displaying said image on said video means.

5. Apparatus as in claim 1 wherein said instrument is rotatably attached to a fixture of relatively large diameter, said imaging system being located within said fixture, said fixture being fixedly attached to an elongated portion having dimensions for fitting a human hand.

6. Apparatus as in claim 5 wherein said imaging system includes video means for viewing the image produced by said imaging system.

7. Apparatus as in claim 6 wherein said imaging system includes a camera for capturing said image and means coupled to said camera for displaying said image on said video means.

8. Apparatus as in claim 6 wherein said elongated portion has a proximal end, said proximal end having extended therefrom a chamber portion including said imaging system, said chamber portion having said hollow instrument axially aligned therewith.

9. Apparatus as in claim 8 also including fluid injection means for introducing fluid into a target area of hair follicular units for increasing the distances therebetween.

10. Apparatus as in claim 8 also including suction means for removal of an excised follicular unit.

11. Apparatus as in claim 5 also including means for positioning said elongated portion with respect to a selected follicular unit.

12. A method of harvesting follicular units of hair for implanting, said method comprising the steps of positioning a hollow instrument having a cutting edge with a diameter about equal to the diameter of critical anatomical parts of a follicular unit of hair over a target donor area of a scalp, aligning said instrument with the axis of a follicular unit to be excised, inserting said instrument into the scalp about a selected follicular unit, advancing said instrument to cut the scalp about the selected follicular unit, and removing said follicular unit.

13. A method as in claim 12 wherein said step of aligning comprises capturing an image of said selected follicular unit, displaying said image on a television screen, and positioning said instrument along the axis of said selected follicular unit.

14. A method as in claim 12 including the step of introducing fluid into said scalp at a selected follicular unit for increasing the distances between adjacent follicular units.

15. A method as in claim 12 including the step of creating a suction for removal of a selected follicular unit.

16. A method of harvesting follicular units of hair for implanting, said method comprising the steps of positioning a hollow instrument having a cutting edge with a diameter about equal to the diameter of critical anatomical parts of a follicular unit of hair over a target donor area of a scalp, aligning said instrument with the axis of a follicular unit to be excised, inserting said instrument into the scalp about a selected follicular unit, advancing said instrument to cut the scalp about the selected follicular unit, and removing said follicular unit, wherein said step of aligning comprises capturing an image of said follicular unit, displaying said image on a television screen, and positioning said instrument along the axis of said follicular units.

17. A method of harvesting follicular units of hair for implanting, said method comprising the steps of positioning a hollow instrument having a cutting edge with a diameter about equal to the diameter of critical anatomical parts of a follicular unit of hair over a target donor area of a scalp, aligning said instrument with the axis of a follicular unit to be excised, inserting said instrument into the scalp about a selected follicular unit, advancing said instrument to cut the scalp about the selected follicular unit, and removing said follicular unit, said method including the step of introducing fluid into said scalp at a selected follicular unit for increasing the distances between adjacent follicular units.

* * * * *